United States Patent
Sano et al.

(12) 
(10) Patent No.: US 6,326,010 B1
(45) Date of Patent: Dec. 4, 2001

(54) PLASTIC VESSEL CONTAINING AN ALBUMIN PREPARATION

(75) Inventors: Minoru Sano; Yoshihisa Hama; Toshiya Kai; Masakazu Mameta, all of Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/695,215

(22) Filed: Oct. 25, 2000

Related U.S. Application Data

(62) Division of application No. 09/400,000, filed on Oct. 20, 1999, now Pat. No. 6,197,936.

(30) Foreign Application Priority Data

Oct. 21, 1998 (JP) .................................................. 10-299829

(51) Int. Cl.[7] .............................. A61J 1/05; A61K 38/38; C07K 14/765

(52) U.S. Cl. ...................... 424/400; 206/438; 206/524.1; 264/525; 422/41; 514/21; 530/363; 604/403; 604/415

(58) Field of Search .................................. 530/362, 363, 530/364, 365, 366, 367, 368, 369, 427; 514/2, 12, 21; 424/400; 422/41; 604/403, 415, 416, 903; 206/438, 524.1; 215/43, 247; 264/524, 525, 571

(56) References Cited

U.S. PATENT DOCUMENTS

| | | | |
|---|---|---|---|
| 3,464,085 | 9/1969 | Burkett et al. | 425/524 |
| 3,957,168 | 5/1976 | Shine et al. | 206/525 |
| 4,049,033 | 9/1977 | Ralston, Jr. et al. | 105/5 |
| 4,191,231 | 3/1980 | Winchell et al. | 150/8 |
| 4,337,025 | 6/1982 | Pagels et al. | 425/392 |
| 4,505,708 | 3/1985 | Gajewski et al. | 604/408 |
| 5,560,955 | 10/1996 | Izzo et al. | 426/633 |
| 5,649,637 | 7/1997 | Weiler | 215/251 |
| 5,677,424 | 10/1997 | Rucheton et al. | 530/364 |
| 5,691,451 | 11/1997 | Ohya et al. | 530/363 |
| 5,846,930 | 12/1998 | Debart et al. | 514/2 |
| 6,197,936 | * 3/2001 | Sano et al. | 530/363 |

FOREIGN PATENT DOCUMENTS

0559895 A1    9/1993   (EP) .

OTHER PUBLICATIONS

Document Bibliography and Abstract; JP2111728 Publication dated (laid open) Apr. 24, 1990.

* cited by examiner

*Primary Examiner*—Jeffrey E. Russel
(74) *Attorney, Agent, or Firm*—Kubovcik & Kubovcik

(57) ABSTRACT

To provide a plastic vessel containing an albumin preparation which completely restrains formation of thermally denatured albumin, a plastic molded member in a cylindrical shape is extruded in a molten state into opened dies, one end of which is closed in the dies, and a vessel is molded by blowing a compressed gas into the molded member in the dies or by bringing inner portions of the dies into a vacuum state. While the vessel is still disposed in the dies, an albumin preparation is introduced from an opening portion into an inner portion of the vessel and, therefore, the albumin preparation can be filled into the vessel in a sterilized state without being brought into contact with the atmosphere. Then, an opening portion of the vessel filled with the albumin preparation is hermetically sealed at an internal temperature of the opening portion of about 40 to 70° C. Thus formation of thermally denatured albumin can be completely restrained.

6 Claims, 7 Drawing Sheets

PLASTIC VESSEL CONTAINING AN ALBUMIN PREPARATION

This application is a division of application Ser. No. 09/400,000 filed Oct. 20, 1999, now U.S. Pat. No. 6,197,936.

FIELD OF THE INVENTION

The present invention relates to a plastic vessel containing an albumin preparation and, particularly, to a vessel capable of stably containing an albumin preparation, in which entry of impurities is eliminated and formation of thermally denatured albumin is completely restrained, and to a method for producing said vessel.

BACKGROUND OF THE INVENTION

Albumin, particularly human serum albumin, is a protein mostly included in blood plasma, and which is produced in the liver and functions to maintain normal osmotic pressure in blood flow, to couple with a nutrient or a metabolite to transport them thereby and so on. Accordingly, albumin is regarded as effective in treatment of symptoms related to trauma of hemorrhagic shock patients, burn injury patients or the like, or patients suffering from hypoalbuminemia or fetal erythroblastosis.

Conventionally, albumin is prepared by fractionating blood collected from human beings, and the albumin preparation is commercially available as a curative reagent, for example, as "ALBUMIN GC" (Yoshitomi Pharmaceutical Co. Ltd.). Further, in recent years, mass production of albumin by gene manipulation has been attempted, and research and development of purification technology have progressed, and a curative reagent manufactured by genetic recombinant technology is expected to be sold.

There is concern about undesirable substances such as hepatitis virus and the like contaminating an albumin derived from blood plasma and, therefore, there has normally been produced an albumin free of impurities by carrying out heat treatment of an aqueous albumin solution. Further, in albumin manufactured by gene recombinant technology, there may be included impurities which are foreign to homo organisms and problematic in antigenicity such as proteins derived from host cells, polysaccharides and so on. Therefore, a recombinant albumin is isolated and purified by subjecting a culture solution including these impurities to a heat treatment. It is known that when such an unpurified albumin is subjected to a heat treatment, the albumin is coagulated with contaminant proteins which are thermally unstable and in JP-A-7-330626 there is described a method of removing such a coagulated albumin. Further, a problem has recently been developed in which a certain kind of thermally denatured albumin of which the molecular structure is unknown brings about an abrupt symptom referred to as anaphylactic shock.

Meanwhile, a conventional vessel containing an albumin preparation has been made of glass, into which the albumin preparation is introduced from an opening of the vessel, which is thereafter hermetically sealed by means of rubber plug or the like. However, according to the method of introducing the albumin preparation into the vessel, there is a danger of bacteria in the atmosphere or other contaminant substances contaminating the albumin preparation in the vessel. When a heat treatment is carried out in a purifying procedure of the albumin preparation, the contaminant substances expedite formation of thermally denatured albumin. As a result, the effects produced by the albumin per se are reduced.

Accordingly, it is preferable to carry out the introduction of an albumin preparation into an inner portion of a vessel and to hermetically seal an opening of the vessel in a system which is not brought into contact with contaminant substances in the atmosphere. Recently, the substitution of glass vessels with plastic vessels has been attempted, but plastic vessels containing an albumin preparation having sufficient functions have not been obtained because of thermal denaturing of the albumin by the heat of hermetical sealing.

As a result of various investigations of albumin preparation vessels which completely restrain formation of thermally denatured albumin, the inventors have found that such complete restraining is achieved by introducing an albumin preparation into a plastic vessel in a system which is not brought into contact with contaminant substances in the atmosphere and by hermetically sealing an opening of the vessel at relatively low temperatures, and reached the invention.

SUMMARY OF THE INVENTION

It is an object of the present invention to provide an albumin preparation vessel in which formation of thermally denatured albumin is completely restrained.

That is, according to an aspect of the invention, there is provided a plastic vessel containing an albumin preparation comprising a main body and a head portion thereon, wherein the main body accommodates an albumin preparation and the head portion is formed by hermetical sealing an opening of the plastic vessel.

According to another aspect of the invention, there is provided a plastic vessel containing an albumin preparation, wherein the vessel is produced by arranging a parison at an inner portion of a pair of body dies, blowing a compressed gas into an inner portion of the parison to form a main body of a plastic vessel, introducing an albumin preparation through an opening into an inner portion of the plastic vessel while the vessel is still disposed in the dies, and hermetically sealing the opening of the plastic vessel to form a head portion.

In another embodiment of the present invention, there is provided a plastic vessel containing an albumin preparation, wherein the vessel is produced by arranging a parison at an inner portion of dies, producing a vacuum in the inner portion of the dies to form a main body of a plastic vessel, introducing an albumin preparation through an opening into an inner portion of the plastic vessel while the vessel is still disposed in the dies, and hermetically sealing the opening of the plastic vessel to form a head portion.

Further, there is provided a plastic vessel containing an albumin preparation, produced according to the above-described aspects of the invention, wherein a rubber-like elastic member is fixedly attached to a head portion of the plastic vessel.

Further, there is provided a plastic vessel containing an albumin preparation, produced according to the above-described aspects of the invention, wherein D/L, which is a ratio of a length D of a neck portion of the main body to a length L of a body portion of the main body, falls in a range of 0.1 to 0.5.

Another aspect of the present invention is a method for producing a plastic vessel containing an albumin preparation which comprises (1) melting a plastic material and forming a parison, which is a plastic member in a cylindrical shape having one closed end, (2) arranging the parison in an inner portion of a pair of body dies, (3) blowing a compressed gas into an inner portion of the parison or applying a vacuum to the inner portion of the pair of body dies to form a main body of a plastic vessel, (4) introducing an albumin preparation through an opening, or opening portion, into an inner portion of the main body of the plastic vessel while the vessel is arranged in said dies, and (5) hermetically sealing the opening portion of the plastic vessel by pressing with a pair of head dies to form a head portion.

DETAILED DESCRIPTION OF THE INVENTION

Figure 1A:
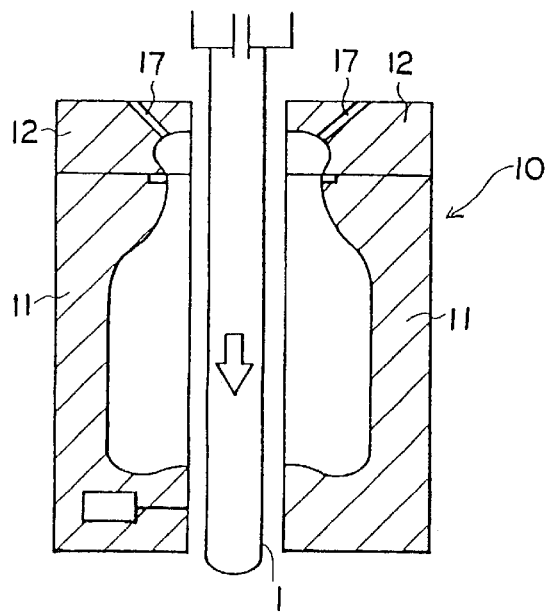
FIGS. 1A, 1B, 2C, 2D, 3E and 3F are explanatory views showing an embodiment of producing an albumin preparation vessel according to the present invention.

The albumin preparation is an aqueous solution obtained by dissolving serum albumin or albumin manufactured by gene manipulation, the molecular weight of which is generally about 67,000, in purified water. Albumin content in the aqueous solution is preferably 0.1 to 30% (W/V). The albumin preparation can include a stabilizing agent of acetyl tryptophan, and an organic carboxylic acid having a carbon number of 6 to 18 or its salt. The amount of the stabilizer, for instance, acetyl tryptophan is preferably 20 to 60 mg per 1 g of albumin dissolved in the albumin preparation. As an organic carboxylic acid having a carbon number of 6 to 18, caproic acid, caprylic acid, capric acid, lauric acid, palmitic acid or oleic acid is exemplified and as their salts, a salt of an alkali metal such as sodium or potassium and a salt of an alkaline earth metal such as calcium are included.

The present vessel filled with an albumin preparation is thermally sterilized as necessary to thereby inactivate virus which may have entered into the albumin preparation. As a sterilizing temperature to prepare the albumin preparation, about 40 to 60° C. is preferable, and a heating period is preferably about 5 to 20 hours.

As a plastic material of the albumin preparation vessel, a material having a capability of tolerating the sterilizing temperature as well as the hermetical sealing of an opening portion of the vessel at an internal temperature of the opening portion of 40 to 70° C. by pressing with head dies is preferred. Such plastic material includes polyolefins such as polyethylene or polypropylene, polyvinyl chloride and ethylene-vinyl acetate copolymer. Specifically, a polyolefin such as polyethylene having a melting point of 90 to 140° C. and a density of 0.890 to 0.940 is preferred.

A method for producing a plastic vessel containing an albumin preparation according to the present invention comprises (1) melting a plastic material and forming a parison, which is a plastic member in a cylindrical shape having one closed end, (2) arranging the parison in an inner portion of a pair of dies, (3) blowing a compressed gas into an inner portion of the parison or applying a vacuum to the inner portion of the pair of body dies to form a main body of a plastic vessel, (4) introducing an albumin preparation through an opening portion of the plastic vessel into an inner portion of the plastic vessel, and (5) hermetically sealing the opening portion of the plastic vessel by pressing with a pair of head dies to form a head portion.

According to the method for producing an albumin preparation vessel of the present invention, a plastic molded material is extruded in a cylindrical form in a molten state into a pair of divided body dies and one end of the plastic molded member in the cylindrical shape is closed in the body dies. A main body portion is molded by means of blowing compressed gas into an inner portion of the molded member, or bringing the inner portions of the body dies into a vacuum state while the molded member still remains in the body dies. Then, the albumin preparation is introduced through an opening portion into an inner portion of the vessel and therefore, the albumin preparation can be filled in an aseptic condition without being brought into contact with the atmosphere. Further, by cooling the body dies, the vessel body is also rapidly cooled. Then, the opening portion of the vessel filled with the albumin preparation is hermetically sealed by pressing with head dies and at this time the head portion of the vessel is cooled by the cooled head dies and therefore, formation of thermally denatured albumin can be completely restrained.

The albumin preparation vessel of the present invention is a cylindrical vessel made of the above plastic having a head portion formed by thermally sealing an open end which is disposed in the upper position. A horizontal section of the vessel main body or the opening portion thereof is preferably circular, elliptical, or approximately guadrangular. The vessel has an oblique portion by which the contents are easily drained towards the head portion and which is disposed in the upper position of the cylindrical vessel, and which is called a shoulder portion, and a neck portion thereon. Optionally, the vessel is provided with a flange that is formed on the neck portion in the molding process. Ahead portion is provided on the upper portion of the vessel body or the flange. In the present invention it is characteristic that the head portion of the vessel is molded from the same plastic resin as the vessel main body and is formed by sealing the opening portion.

In an albumin preparation vessel of the present invention, a ratio (D/L) of a length D of a neck portion of the main body to a length L of the body portion of the main body falls in a range of preferably 0.1 to 0.5, more preferably 0.1 to 0.3, and most preferably 0.1 to 0.15. An albumin preparation has a probability of being susceptible to heat in a D/L ratio of the vessel of less than 0.1, and the vessel does not balance in a D/L ratio of more than 0.5. The length D of a neck portion of the vessel means a distance from an upper shoulder to an opening portion, preferably a flange, and the length L of the body portion of the main body means a distance from a bottom of the vessel to the shoulder portion.

A ratio of the area of a horizontal section of the main body to that of opening portion of the vessel is preferably 0.01 to 0.5, more preferably 0.1 to 0.2, and most preferably 0.1 to 0.15, and differs depending on the amount of the albumin preparation accommodated therein.

The size of the albumin preparation vessel in the present invention is also different according to the amount of the albumin preparation accommodated therein. Specifically, the diameter of a circular section of a cylindrical main body is preferably 10 to 150 mm, more preferably 50 to 100 mm, and most preferably 60 to 80 mm. The ratio of long axis to short axis in an elliptical section of a main body is preferably more than 1, more preferably 1.5 to 5.0, and most preferably 2.0 to 3.0. Further, the ratio of longitudinal length to width in a quandrangular section of a main body is preferably more than 1.1, more preferably 1.5 to 5.0, and most preferably 2.0 to 3.0. Additionally, the wall thickness of the main body is usually 0.2 to 2.5 mm, preferably 0.3 to 1.5 mm, and most preferably 0.4 to 0.7 mm. And the wall thickness of the neck portion is usually 0.3 to 3.0 mm, preferably 0.8 to 2.0 mm, and most preferably 1.0 to 1.5 mm. The wall thickness controls the internal temperature of the vessel, and even if the temperature of the dies is constantly maintained, the internal temperature of the vessel varies with the wall thickness of the various parts. As the internal temperature of the shoulder especially tends to be increased compared with other parts, it is necessary to devise cooling circuits so as to increase the efficiency of cooling of the molding dies.

An opening portion, or opening, of the albumin preparation vessel in the present invention means an opening portion for accommodating the albumin preparation in the vessel. The opening portion is made of the same plastic resin as the main body and is a portion to be hermetically sealed by pressing with head dies to form a head portion of the vessel.

Conventionally, in order to make a head portion metal plates are installed at both sides of an opening portion of a plastic vessel. A plastic lid is positioned on the top of the opening portion, and then the metal plates are heated to warm the plastic lid and the opening portion. After the metal plates are removed, the remaining part of the lid and the opening portion are thermally adhered. However, such method to make the head portion of the vessel has a problem that albumin is denatured by the heated metal plates. On the contrary, albumin is not denatured in the present invention, because the opening portion formed of the same plastic as the main body of the vessel is adhered by pressing with head dies at relatively low temperatures to form a head portion.

A device for producing the instant albumin preparation vessel is exemplified by a blow fill seal system such as "Bottelpack" manufactured by ROMMELAG, but is not limited to this device.

The process for producing the vessel comprises the following steps.

(1) The plastic material is heated at a temperature of more than its melting point, and the melted product is extruded with an extruder having a tubular orifice so as to be dropped down, or lowered, between open divided dies and form a plastic member in a cylindrical shape having one closed end.

(2) The above melted plastic member in a cylindrical shape is dropped down, or lowered, by gravity between the open divided dies which consists of body dies and head dies. The temperatures of the body dies and the head dies are usually controlled at about 5 to 30° C., and therefore, the plastic member in a cylindrical shape dropped down in a molten state is cooled down to about 100 to 150° C., (3) Compressed gas such as an air is introduced in an opening portion of the plastic member in order to inflate the plastic member to form a main body of the vessel in contact with the body dies. The temperature of the main body of the plastic member is decreased to about 40 to 70° C. because the temperature of the body dies, as noted above, is usually controlled at about 5 to 30° C. On the other hand, the upper position of the plastic member not in contact with the body dies is maintained at about 100 to 150° C.

A main body of a plastic vessel can also be formed by means of a vacuum applied to the inner portion of the dies in a conventional way. The opening portion which is located on the plastic member in a cylindrical shape but is not contacted with the body dies is usually at a state of the temperature of about 100 to 150° C. in this step.

(4) The albumin preparation is introduced through the opening portion into the inner portion of the vessel as soon as possible after the vessel is molded from the above plastic member. The temperature of the main body of the vessel is about 10 to 60° C. after the introduction of the albumin preparation since the temperature of the albumin preparation introduced is commonly about 5 to 25° C. However the internal temperature of the opening portion of the vessel is still maintained at about 50 to 90° C.

(5) Then, the opening portion of the vessel accommodating the preparation is sealed by pressing with the head dies. It is desirable to press with the head dies at an internal temperature of the opening portion of the vessel of about 40 to 70° C. Sealing the opening portion by pressing with the head dies is difficult at an internal temperature of the opening portion of less than 40° C. after molding the vessel. Further, the albumin preparation accommodated therein may be denatured when the opening portion is sealed at an internal temperature of more than 70° C.

The following is an example of a method for producing an albumin preparation vessel according to the present invention with reference to the drawings. FIGS. 1A, 1B, 2C, 2D, 3E and 3F are explanatory views illustrating an example of producing an albumin preparation vessel according to the invention.

Figure 1B:
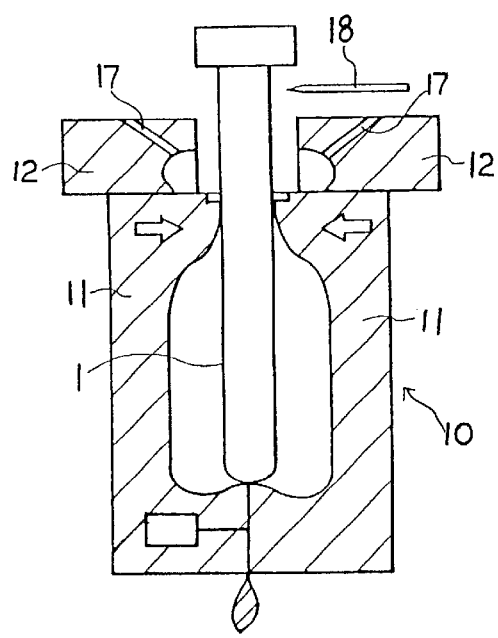

Divided dies 10 used in blow-molding a plastic molded member 1 having a cylindrical shape comprise a pair of left and right main body dies 11 and a pair of left and right head dies 12. First, a plastic molded member (parison) 1 having a closed lower end is dropped down between the divided dies 10 in a state in which the divided dies 10 are opened before blow-molding (FIG. 1A). The parison 1 may be fabricated by extruding plastic from an extrusion nozzle or a parison formed beforehand may be heated in the dies. Next, the main body dies 11 are tightly closed and the parison 1 is cut by a heated knife 18 at a position above the divided dies 10 (FIG. 1B). The temperatures of the body dies and head dies are controlled at temperature of about 5 to 30° C.

Figure 2C:
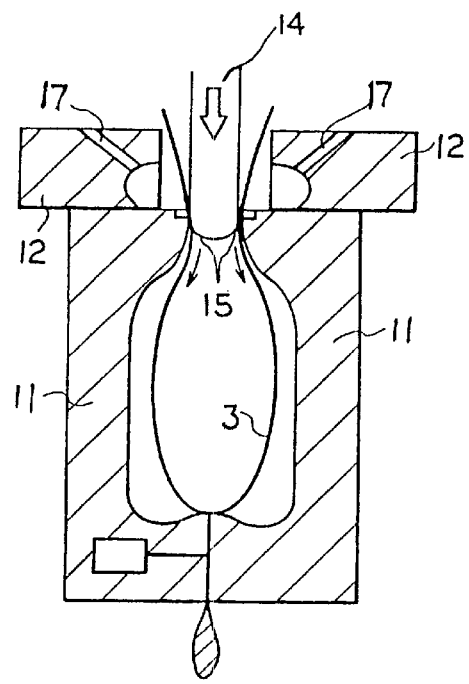

A mandrel 14 is pushed down from an upper opening portion 2 of the parison 1 heated at about 100 to 150° C. The mandrel 14 is provided with air blow holes 15. After pushing down the mandrel 14 into the main body dies 11, compressed air is injected from the air blow holes 15 into the parison 1 to thereby expand the parison 1 to a predetermined shape. The upper portion of the expanded parison is called an opening portion (FIG. 2C). Next, a front end of an albumin preparation injecting nozzle 16 arranged in the mandrel 14 is lowered to a position at a vicinity of a bottom portion of vessel main body 3 and an albumin preparation is introduced from the nozzle 16. At this step, air inside of the vessel main body 3 is exhausted from the air blowholes 15 (FIG. 2D).

Figure 3E:
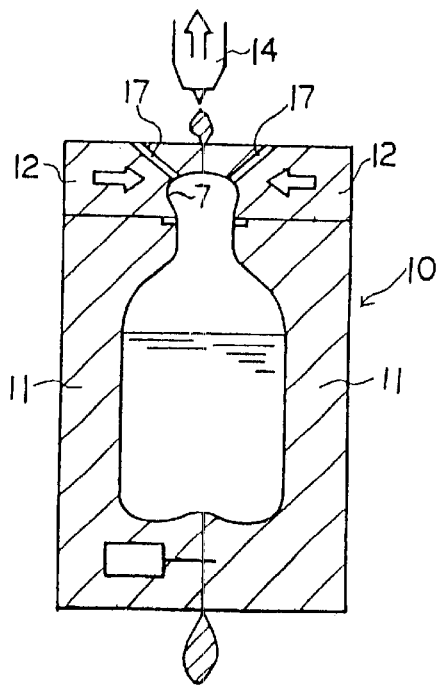
Figure 3F:
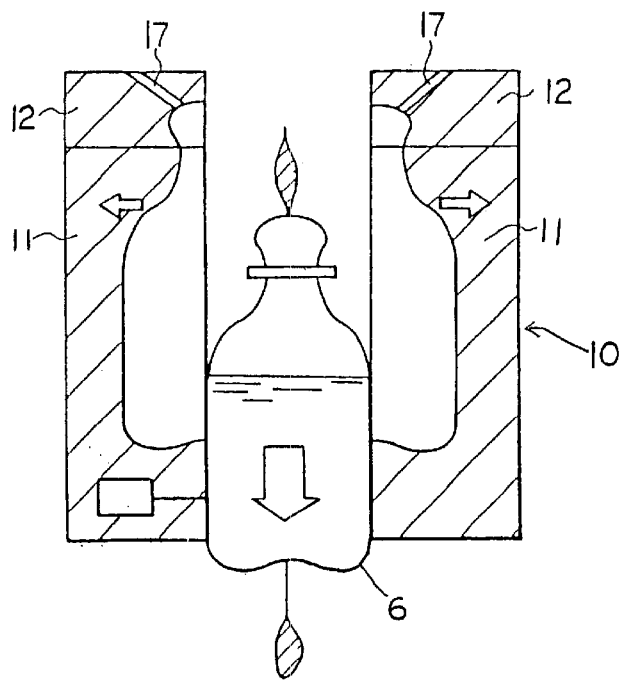

After filling the albumin preparation into the vessel main body 3, the nozzle 16 is retracted into the mandrel 14 and the mandrel 14 is removed from the divided dies 10. Thereafter, the head dies 12 are tightly closed. A plurality of sucking holes 17 are provided at inner walls of the head dies 12 and a vessel head portion 7 disposed between the head dies 12 is molded by vacuum and simultaneously therewith the vessel opening portion 5 (not shown) is hermetically sealed (FIG. 3E). The internal temperature of the plastic member in a cylindrical shape(opening portion) located near the head dies 12 at this occasion falls in a range of around 40 to 70° C., preferably 40 to 60° C. When the temperature of the opening portion exceeds 70° C., there is a concern that the albumin preparation filled in the vessel main body 3 will be heated and thermally denatured albumin will be formed. And when the internal temperature of the opening portion is less than 40° C., there is a tendency that the vessel-opening portion 5 is difficult to be completely hermetically sealed. Next, the divided dies 10 are opened and vessel 6 containing the albumin preparation is taken out from the divided dies 10 (FIG. 3F).

Figure 4:
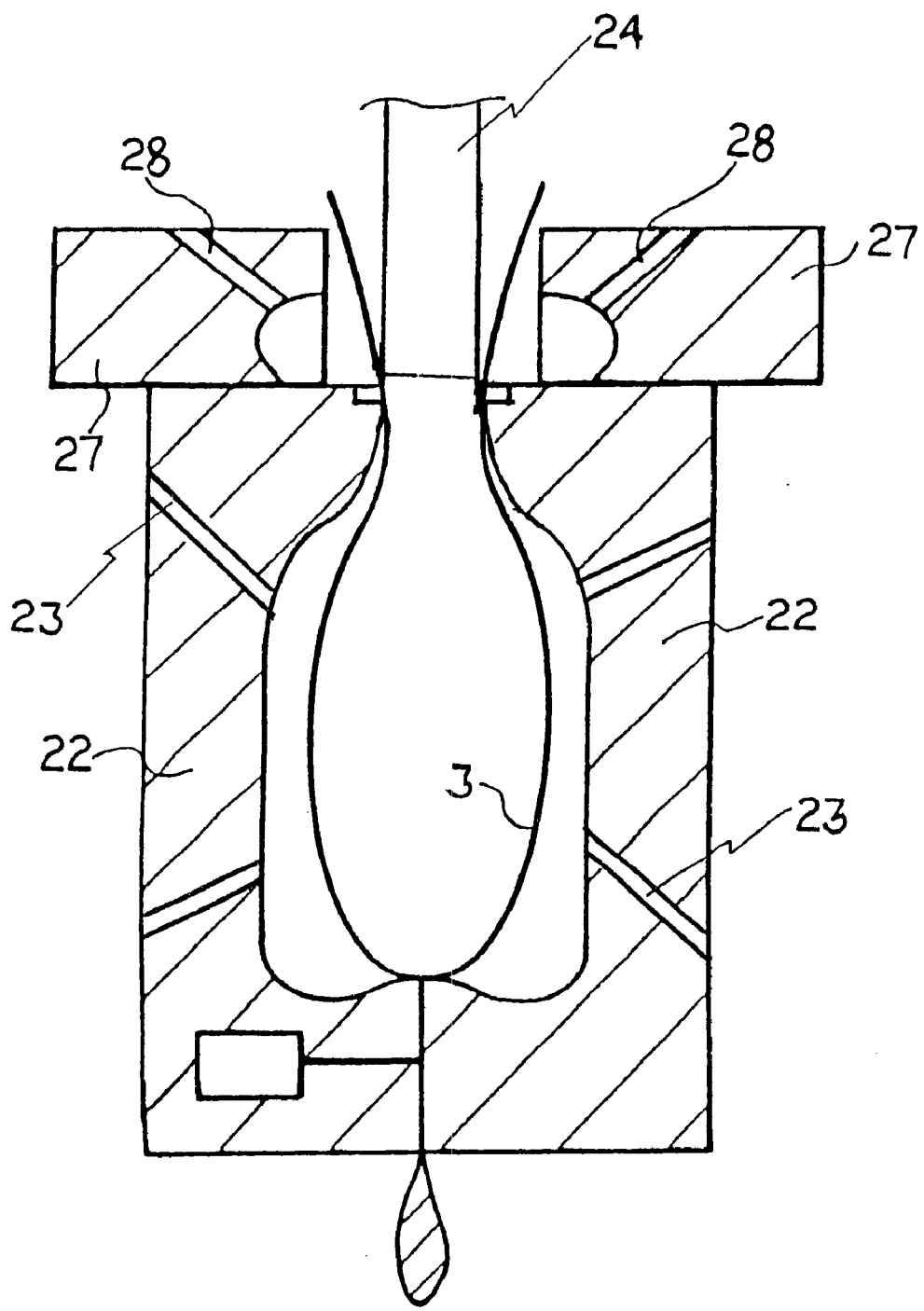
FIG. 4 is an explanatory view showing another embodiment of producing an albumin preparation vessel according to the present invention.

An explanation will be given of another example, or embodiment, of preparing an albumin preparation vessel according to the present invention with reference to FIG. 4. FIG. 4 is an explanatory view in a case in which a plastic molded member (parison) in a cylindrical shape and in a molten state is sucked by a plurality of sucking holes 23 provided at inner walls of main body dies 22 and is formed under a vacuum into a predetermined shape corresponding to the shapes of the main body dies 22. The parison having a closed lower end inserted between the divided dies is fixed by the closed main body dies 22 and subjected to a vacuum by the plurality of sucking holes 23 provided at the inner walls of the main body dies 22. The parison is formed into the shapes of the main body dies 22 to thereby form the vessel main body 3. A plurality of sucking holes 28 are provided also at inner walls of head dies 27 which are opened. A front end of a mandrel 24 is inserted into an opening portion of the parison and similar to the step illustrated in FIG. 3E, a vessel head portion is also formed by vacuum forming.

Figure 2D:
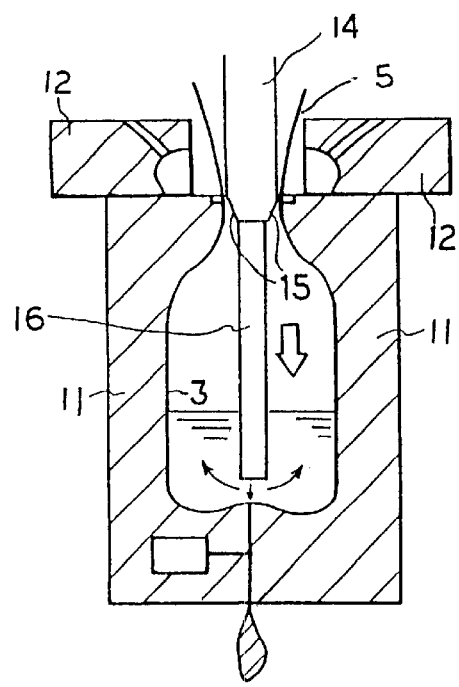

Next, according to the procedure illustrated in FIG. 2D, an albumin preparation is introduced from an albumin preparation injecting nozzle arranged in the mandrel into the vessel main body and the mandrel is discharged from the divided dies. Thereafter, according to a procedure as shown by FIG. 3E, the head dies are closed tightly, the parison is sucked under a vacuum from the plurality of the sucking holes provided at the inner walls of the head dies to form the vessel head portion and the vessel opening portion is hermetically sealed. The internal temperature of the opening portion falls in a range of about 40 to 70° C. at this time. Next, the divided dies are opened and the vessel containing the albumin preparation is taken out from the divided dies.

Figure 5:
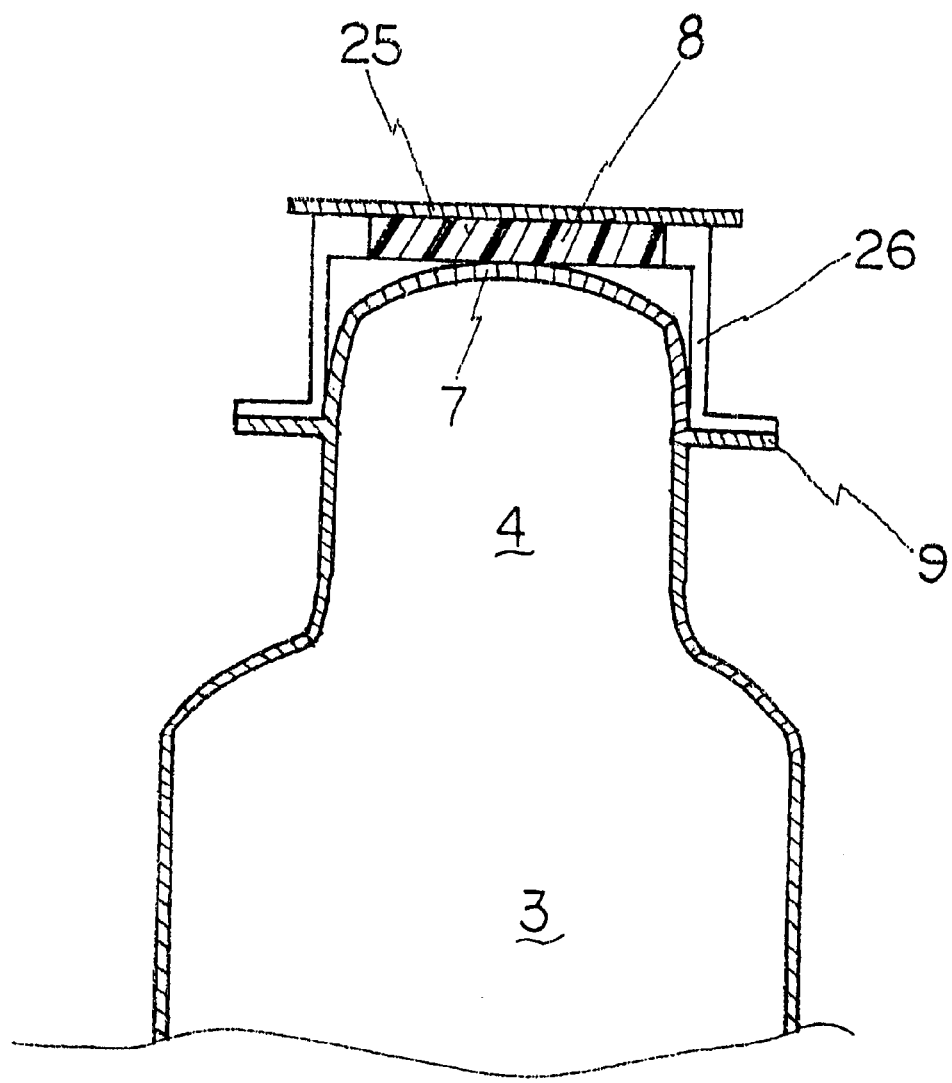
FIG. 5 is a partially sectional view showing an embodiment of an albumin preparation vessel according to the present invention.

FIG. 5 is a partially sectional view showing another embodiment of an albumin preparation vessel according to the present invention, in which a rubber-like member 8 is fixedly attached onto an upper face of the vessel head portion 7. A flange 9 projected outwardly in the diameter direction is formed at an outer peripheral face of the head portion 7 and welded to a bottom end of a caulking member 26 and the rubber-like elastic member 8 is fixedly attached to the vessel head portion 7. A thermally shrinkable protection film 25 is covered on an outer face of the rubber-like elastic member 8 to prevent contaminating substances in the atmosphere from attaching thereto. As a material of the rubber-like elastic member 8, synthetic rubber such as butyl rubber, polyisobutylene rubber, silicone rubber and ethylene/polypropylene rubber, or a natural rubber is included. When the rubber-like elastic member 8 is fixedly attached onto the upper face of the head portion 7 of the albumin preparation vessel and a piercing needle pierces the rubber-like elastic member 8 and the head portion 7, a recovery force is exerted on the needle hole pierced into the rubber-like elastic member in a direction of closing of the needle hole and, therefore, the piercing needle is brought into contact with the needle hole and the albumin preparation is prevented from leaking to the outside. Although a plastic material such as polyolefin, polyester and polyamide is preferable as a material of the caulking member 26, a metal such as aluminum and stainless steel or ceramic can also be used.

Figure 6:
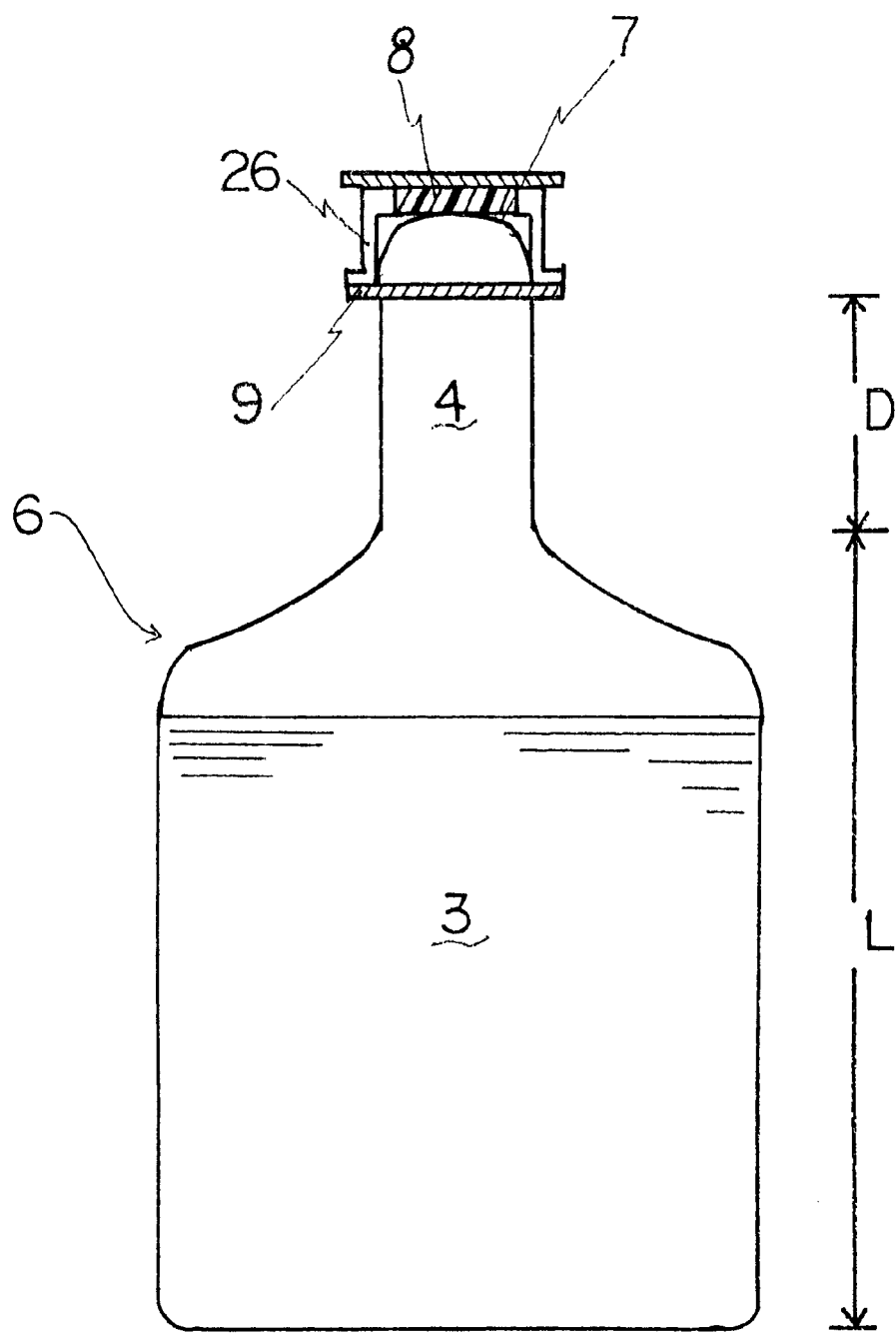
FIG. 6 is an explanatory view showing another embodiment of an albumin preparation vessel according to the present invention.

FIG. 6 is an explanatory view showing an embodiment of an albumin preparation vessel according to the invention. The rubber-like elastic member 8 is fixedly attached onto the upper face of the vessel head portion 7 of the vessel 6 containing the albumin preparation in the vessel main body 3 by means of the caulking member 26. When the caulking member 26 is made of plastic material, the flange 9 is heated to temperature in a range of about 300 to 450° C. and welded to a projected portion at a lower end of the caulking member 26 to thereby mount the rubber-like elastic member 8 onto an upper face of the vessel head portion 7. In this case, it is preferable that a length D of the vessel neck portion 4 to a length L of the body portion of the vessel main body 3, that is, D/L, falls in a range of 0.1 to 0.5, preferably 0.1 to 0.3, and most preferably 0.1 to 0.15 such that the temperature of the albumin preparation contained in the vessel main body 3 is not elevated. The vessel neck portion 4 is a straight pipe, or cylindrical member extending from the caulking member 9 of the vessel 6. The lowest end thereof is disposed at a position where the diameter of the vessel starts increasing and its length is represented by notation D. The vessel main body 3 ranges from the lowest end of the vessel neck portion 4 to a bottom portion of the vessel and its length is represented by notation L. When D/L is less than 0.1, there is a danger that a portion of the albumin preparation contained in the vessel main body 3 is thermally denatured by the high temperature at which the caulking member 26 is welded to the flange 9 and when D/L exceeds 0.5, there is a tendency that erection of the vessel 6 becomes unstable.

The caulking member 26 shown in FIG. 6 gives a moderate elasticity to a head portion into which a needle is pierced when the albumin preparation is administered into a human body from the vessel of the present invention, but this member can be substituted with a connector having a luer. Therefore, the present albumin preparation vessel does not necessarily require the caulking member.

An explanation of an example of the invention is illustrated by the following embodiments.

EXAMPLE 1

Low-density polyethylene (made by Nippon Yunika Co. Ltd., DEFD-1137) having a density of 0.906 g/cm$^3$ was melted and extruded from an extrusion nozzle in a cylindrical shape at an extrusion temperature of 190° C. to thereby fabricate a cylindrical molded member (parison) one end of which is closed. The parison was lowered between the divided dies 10 (FIG. 1A) and the main body dies 11 were closed tightly (FIG. 1B). Next, the mandrel 14 was pushed down from the upper opening portion of the parison 13 and pressurized air was blown with a pressure of 3 kg/cm$^2$ to thereby form the vessel main body 3. The temperature of the main body dies 11 at this point was about 50° C. (FIG. 2C). Thereafter, a front end of the preparation injecting nozzle 16 was lowered to the bottom portion of the vessel main body 3 and 250 ml of a 5% aqueous albumin solution (BUMINATE ALBUMIN, produced by Baxter Healthcare) was introduced into the vessel main body 3 (FIG. 2D). Then, the preparation injecting nozzle 16 was retracted, the head dies 12 were closed tightly at an internal temperature of the opening portion 5 of 40° C., the vessel head portion 7 was molded under vacuum by being sucked from the sucking holes 17 and the vessel opening portion 5 was hermetically sealed (FIG. 3E).

Three albumin preparation vessels having a similar shape were produced at various internal temperatures of the opening portion in the above procedure.

Floating components in the contents were measured by transmission light of 8,000 to 10,000 luces before and after heat treatment at 60° C. for 10 hours after producing the albumin preparation vessel. The results are shown in Table 1.

TABLE 1

|  | Sample 1 present invention | | Sample 2 comparative example | | Sample 3 Comparative example | |
| --- | --- | --- | --- | --- | --- | --- |
| Temperature of Head dies (° C.) | 6 | | 30 | | 40 | |
| Internal temperature of Opening portion (° C.) | 40 | | 75 | | 85 | |
| Thickness of main body (mm) | 0.6 | | 0.6 | | 0.6 | |
| Samples (number) | 15 | | 15 | | 15 | |
| Formation of denatured products | before *¹ after *² | 0/15 0/15 | before *¹ after *² | 2/15 5/15 | Before *¹ after *² | 5/15 10/15 |

*¹ before heat treatment, *² after heat treatment

Figure 7:
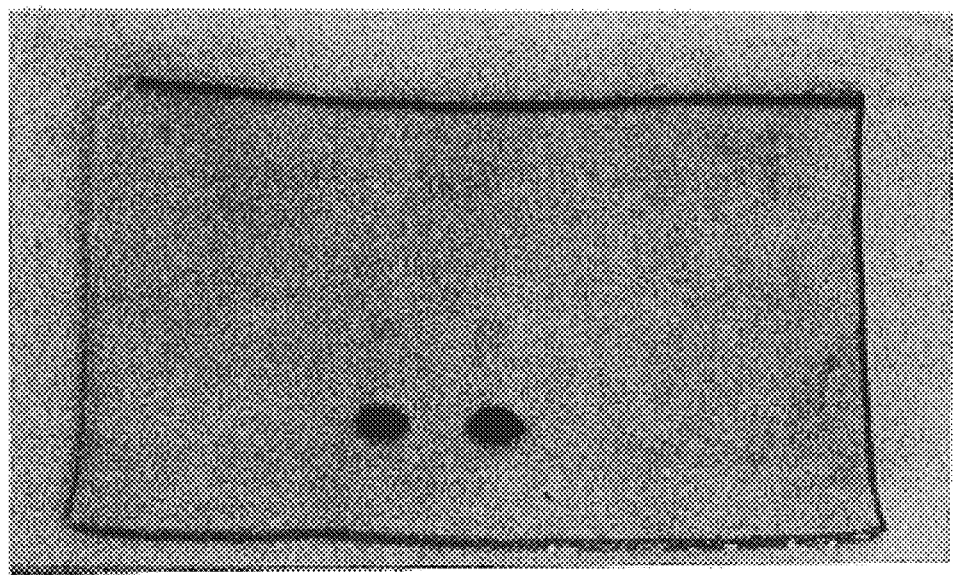
FIG. 7 is an electrophorogram of an albumin preparation before and after accommodation in the albumin preparation vessel of the present invention.

The albumin preparations accommodated in the above vessel and those before the accommodation (sample 1) were determined by PAGE electrophoresis in a conventional way, and thereby the same bands in the electrophoresis gels were found (See, FIG. 7, lane I, before accommodation, lane II, after accommodation). From these data, the albumin preparation accommodated in the vessel seems not to form denatured products.

EXAMPLE 2

A butyl rubber sheet having a thickness of 2 mm was mounted onto the vessel head portion 7 which was exposed by opening the head dies 12 shown in FIG. 3E. The flange 9 of FIG. 5 was heated by hot air at 400° C. and was welded to the lowest end of the caulking member 26 to thereby fixedly attach the butyl rubber sheet onto the vessel head portion 7. The formation of denatured products in the contents is determined by the transmission light.

According to the method of producing an albumin preparation vessel of the present invention, a plastic molded member in a cylindrical shape (parison) is molded by being extruded into a pair of opened dies in a molten state, one end of the parison is closed in the dies, a main body is molded by blowing compressed gas into the molded member in the dies or bringing the inner portions of the dies into a vacuum state. During a time period in which the molded member is still disposed in the dies, the albumin preparation is introduced into the vessel from the opening portion of the molded member and therefore, the albumin preparation can be filled thereinto in a sterilized state without being brought into contact with the atmosphere. Further, the opening portion of the vessel filled with the albumin preparation is hermetically sealed at an internal temperature of the opening portion in a range of 40 to 70° C. and accordingly, formation of thermally denatured albumin can be completely restrained.

Furthermore, it is a remarkable unexpected effect that a labile protein such as albumin can be accommodated in the plastic vessel simultaneously with the production of the plastic vessel and that denaturation of the protein is suppressed.

What is claimed is:

1. A plastic vessel containing an aqueous serum albumin preparation and comprising a main body and a head portion thereon, said main body and head portion being formed of the same plastic material and said main body having a body portion, a shoulder portion and a neck portion, the neck portion being a cylindrical member, wherein the main body accommodates said aqueous serum albumin preparation and the head portion is formed by being hermetically sealed at an opening portion of the plastic vessel and wherein D/L, where D is a length of the neck portion of the main body and L is the length of the shoulder portion and body portion of the main body, is 0.1 to 0.5.

2. A plastic vessel according to claim 1, wherein said vessel is produced by arranging a parison of molten plastic having one closed end at an inner portion of a pair of mold dies, blowing a compressed gas into an inner portion of the parison to form a main body of a plastic vessel, introducing the aqueous serum albumin preparation through an opening portion into an inner portion of the plastic vessel while the vessel is arranged in said dies, and hermetically sealing the opening portion of the plastic vessel to form a head portion.

3. A plastic vessel according to claim 1, wherein said vessel is produced by arranging a parison of molten plastic having one closed end at an inner portion of a pair of mold dies, applying a vacuum to an inner portion of the die to form a main body of a plastic vessel, introducing the aqueous serum albumin preparation through an opening portion into an inner portion of the plastic vessel while the vessel is arranged in said dies, and hermetically sealing the opening portion of the plastic vessel to form a head portion.

4. A plastic vessel according to claim 1, wherein a rubber-like elastic member is fixedly attached to the head portion of the plastic vessel.

5. A plastic vessel according to claim 2, wherein a rubber-like elastic member is fixedly attached to the head portion of the plastic vessel.

6. A plastic vessel according to claim 3, wherein a rubber-like elastic member is fixedly attached to the head portion of the plastic vessel.

* * * * *